(12) United States Patent
Lu et al.

(10) Patent No.: US 8,229,678 B2
(45) Date of Patent: Jul. 24, 2012

(54) METHODS AND SYSTEMS FOR TRANSFORMING PARTICLE DATA

(75) Inventors: Jiuliu Lu, Homestead, FL (US); John Steven Riley, Miami, FL (US); Christophe P. Godefroy, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 945 days.

(21) Appl. No.: 12/180,049

(22) Filed: Jul. 25, 2008

(65) Prior Publication Data

US 2010/0023274 A1 Jan. 28, 2010

(51) Int. Cl.
*G01N 33/48* (2006.01)

(52) U.S. Cl. .......................................... 702/21

(58) Field of Classification Search .............. 702/21, 702/194, 50
See application file for complete search history.

(56) References Cited

U.S. PATENT DOCUMENTS

| 6,954,722 | B2 * | 10/2005 | Parks et al. ................... 702/194 |
| 2006/0259253 | A1 * | 11/2006 | Ellison et al. ................... 702/50 |

OTHER PUBLICATIONS

Ochterski, "Thermochemistry in Gaussian", http://www.gaussian.com/g_whitepap/thermo.htm, Apr. 19, 2000.*
C. Bruce Bagwell, "HyperLog—A Flexible Log-like Transform for Negative, Zero, and Positive Valued Data," Rapid Communication, Cytometry Part A 64A:34-42, 2005.

* cited by examiner

*Primary Examiner* — Jonathan C Teixeira Moffat
*Assistant Examiner* — Xiuquin Sun
(74) *Attorney, Agent, or Firm* — K&L Gates LLP (57) ABSTRACT

In an embodiment, a computer-implemented method is provided for processing data from a particle analyzer. The method includes transforming data using at least one transform that provides: transformation according to a weighted combination of a first mathematical function and a logarithmic function for positive data values, such that the transformation corresponds to the first mathematical function for positive particle data values approaching zero, and to the logarithmic function for positive particle data values approaching infinity; and transformation corresponding to a second mathematical function for negative data values. The transformed data may be then output for display or storage. In another embodiment, the transforming involves substituting the particle data for an independent variable in the transform to directly obtain values to be plotted based on the input particle data values.

9 Claims, 10 Drawing Sheets

Prior Art

METHODS AND SYSTEMS FOR TRANSFORMING PARTICLE DATA

BACKGROUND

The present invention relates generally to the field of particle analyzers, and more specifically to the display and analysis of data collected from particle analyzers.

Particle analyzers enable analysis of properties of particles, for example, individual cells, by subjecting them to an excitation light and measuring the resulting scattered and/or emitted light as detected by one or more light detectors. Different types of particle analyzers, such as flow cytometers and scanning cytometers, are described in the art. In a flow cytometer, for example, the excitation light beams may be stationary, while analyte cells in a liquid flow through a point at which the light beams converge. A scanning cytometer scans a fixed cell population, for example, on a microscope slide, with one or more excitation light beams. Flow cytometers can also be equipped with sorting devices that separate individual cells in a sample for further culture or analysis.

Prior to being exposed to an excitation light, particles may be labeled (also referred to as marked) with spectrally distinct fluorescent dyes or fluorescent dyes conjugated to molecule-specific ligands. In a sample, each particle may bind with one or more fluorescent dyes and/or dye conjugates. For example, a single cell may bind with one or more fluorescent dyes conjugated to antigen-specific antibodies depending on the characteristics of the proteins that are elements of that cell. When an excitation light is focused on a cell in a flow cytometer, the cell may scatter and/or emit light in several directions. The pattern of the scattered and/or emitted light allows one type of cell to be distinguished from another. The resulting fluorescence pattern is generally indicative of defined characteristics of the particles under analysis. Samples of particles are generally labeled with multiple dyes or dye conjugates in order to identify a range of properties of the constituent particles.

A particle analyzer may include multiple light detectors, and dyes are selected so that the peak fluorescence range of each dye is detected by a separate light detector. Due to the very low intensity of the kind of light emitted by small particles, these instruments are generally equipped with very sensitive detectors known as photomultiplier tubes (PMTs) that can detect individual photons. The resulting fluorescence measurements are based on the number of the photons detected by each light detector.

Often, when multiple dye fluorescence is being measured, the particle data contains some noise due to spillover of one fluorescence into another fluorescence range. The degree of spillover varies due to many factors, but in general, as more colors are being measured the noise due to spillover increases. Therefore, in many situations, the particle data is processed to first reduce the noise due to this spillover effect through a process known as compensation. Compensation, attempts to offset an estimated spillover amount from the particle data. Therefore, some particle data values resulting after compensation can be in the negative range.

Due to the large dynamic range of the measured fluorescence signal intensities, often in the range of four log decades or 10,000:1, linear display of a large amount of data would be of little clarity. In general, an exponential curve in the linear domain appears as a linear curve in the logarithmic domain. The logarithmic scale is therefore able to display a large dynamic range such as 10,000:1 and is used very frequently to display and analyze particle data. However, the data may contain a number of negative data points. Mathematically such negative data points are undefined on a logarithmic scale and are often lost or just shown as a collection of points on a display axis, limiting the usefulness of those data points.

Scaling systems, such as the biexponential model (Logicle) display described in U.S. Pat. No. 6,954,722, rely upon display techniques to present a useful display of the data addressing some issues of the pure logarithmic scale display mentioned above. The biexponential model applies a linear scaling for lower intensity data points and a logarithmic scaling for higher intensity data points that alleviates the problem of inability to show negative data points in a pure logarithmic scaled display.

However currently available methods generally require computation-intensive root finding operations and/or the use of lookup tables to determine the value to be used for display based on the particle data (including compensated particle data).

What is needed therefore, are methods and systems to flexibly and efficiently transform particle data in a manner that facilitates display and analysis of that data.

SUMMARY

The present invention relates to particle analysis. In one embodiment, a computer-implemented method for analyzing particle data from a particle analyzer includes transforming the particle data using at least one transform that provides: a first transformation according to a weighted combination of a first mathematical function and a logarithmic function for positive particle data values, and a second transformation corresponding to a second mathematical function for negative particle data values, to generate transformed data. The transformation corresponds to the first mathematical function for positive particle data values approaching zero. The transformed data may be then output for display or storage. In another embodiment, the transforming involves directly substituting the particle data for an independent variable in the transform to obtain values to be plotted based on input particle data values.

Another embodiment is a system for displaying and analyzing particle data. The system includes a computer coupled to a particle analyzer. The computer can have a transforming module that provides transformation according to a weighted combination of a first mathematical function and a logarithmic function for positive particle data values, and transformation corresponding to a second mathematical function for negative particle data values, to generate transformed data. The transformation corresponds to the first mathematical function for positive particle data values approaching zero.

Yet another embodiment is a computer program product to transform particle data from a particle analyzer, having a first computer readable program code that enables the computer to perform: a first transformation according to a weighted combination of a first mathematical function and a logarithmic function for positive particle data values, and a second transformation corresponding to a second mathematical function for negative particle data values, to generate transformed data. The transformation corresponds to the first mathematical function for positive particle data values approaching zero, and to the logarithmic function for positive particle data values approaching infinity.

Further features and advantages of the present invention, as well as the structure and operation of various embodiments thereof, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The features and advantages of the present invention will become more apparent from the detailed description set forth below when taken in conjunction with the drawings. In the drawings, like reference numbers generally indicate identical, functionally similar, and/or structurally similar elements. Generally, the drawing in which an element first appears is indicated by the leftmost digit(s) in the corresponding reference number.

DETAILED DESCRIPTION

The present invention relates to particle data display and analysis. While the present invention is described herein with reference to illustrative embodiments for particular applications, it should be understood that the invention is not limited thereto. Those skilled in the art with access to the teachings herein will recognize additional modifications, applications, and embodiments within the scope thereof and additional fields in which the invention would be of significant utility.

Overview

The particle data (also called "event data") received from a particle analyzer generally comprises a spillover component. The process of compensation that this particle data is commonly subjected to may result in a number of data points in the negative range. Even particle data that is uncompensated may benefit from improved display and analysis methods and systems, because depending on the application (e.g., whether the particle data is primarily low values or high values) the display may be tailored to offer better analysis capability. For purposes of this disclosure, particle data is meant to represent uncompensated particle data as well as compensated particle data or processed particle data, unless a distinction is made clear in the relevant text.

The present invention, in some embodiments, transforms high valued particle data points to conform to a logarithmic function while smoothly transitioning to correspond to a user-definable power function for particle data point values close to zero. With the control of a few configuration parameters, the user may be able to display the data in a way that is particularly helpful to the analysis of a particular sample. For example, some applications may benefit from expanding the value range over which a transform for values close to zero is applied, while other applications with large values may benefit from a wider range of values over which a log transform for large values is applied.

In a further feature, an embodiment also offers a closed form of the transformation that is continuous over the range $(-\infty, +\infty)$. Having a closed form of the transformation over the entire range of possible values gives another highly desirable advantage, i.e., the ability to derive the value to be displayed by substituting a corresponding particle data point in the closed form equation of the transform. The ability to directly compute the value to be displayed based on the input particle data value can offer a level of accuracy and flexibility greater than other display methods that either use lookup tables or complex root-finding operations alone can offer.

System Components

Figure 1:
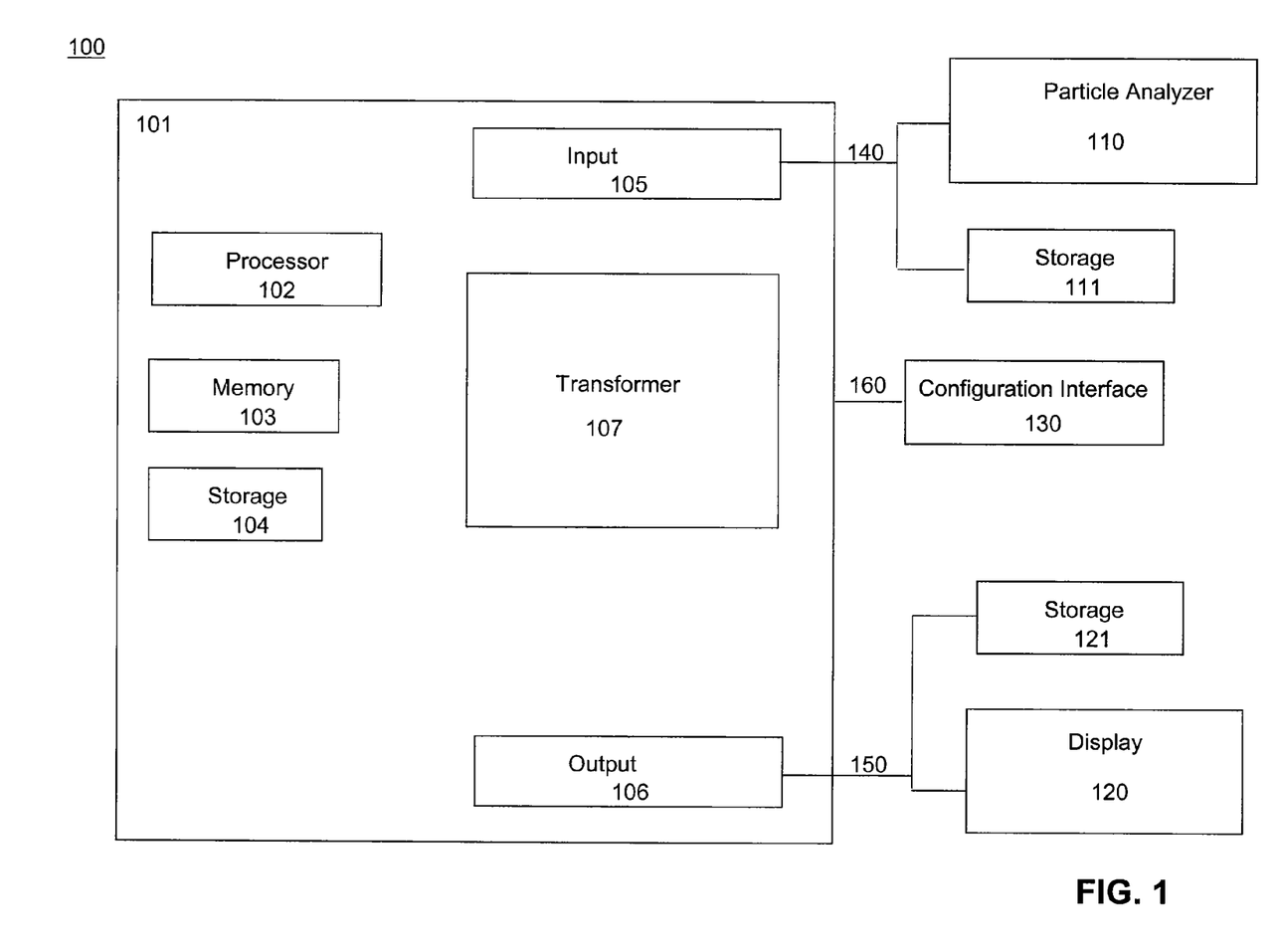
FIG. 1 is a system for transforming particle data, according to an embodiment of the present invention.

FIG. 1 shows a system 100 for processing and analyzing particle data according to an embodiment of the present invention. A computer 101 is coupled through link 140 to a particle analyzer 110 and a storage device 111. Computer 101 is also coupled, through a link 150, to a display device 120 and a storage device 121. Links 140 and 150 may represent communication paths internal to a single computer, or connectivity provided by one or more networks such as a local area network or a wide area network.

Computer 101 may include any type of computing or data processing device. In one example computer 101 includes a processor 102, a memory 103, a storage device 104, an input module 105, an output module 106, and a transformer module 107. Transformer module 107 transforms particle data according to the teachings of this disclosure. The functionality of transformer module 107 is further described below. One skilled in the art will recognize that transformer module 107 may be implemented entirely in software, hardware or using combinations of software and hardware. For example, some of the functionality herein may be implemented with the assistance of a specialized field programmable gate array (FPGA) or digital signal processor (DSP). Logic instructions, including software computer programs implementing some or all of the functionality of modules 105, 106, and 107 may be encoded in a computer usable medium including but not limited to a DVD, a CD-ROM, a floppy disk, a tape, a flash memory device or component, a system memory device or component, or hard drive. Computer 101 may include multiple computing or data processing devices that are located on the same or different platforms at the same or different locations.

Processor 102 may execute all software processing in computer 101, and may also be responsible for the coordination of any hardware components. In another embodiment, computer 101 may include multiple processors for executing software. A memory module 102 may be implemented as random access memory (RAM) and may store execution instructions and data being processed. For example, memory module 103 may hold particle data input to computer 101 during the processing of that data in transformer module 107. An internal storage device 104 may store converted particle data output by transformer module 107. In other embodiments, storage device 104 may serve to temporarily store data being processed by transformer module 107.

Input module 105 and output module 106 may include a combination of hardware and software components enabling computer 101 to receive particle data and to output processed particle data respectively. For example, input module 105 may include a network interface device and the associated software to receive incoming data over link 140 and make that data available to transformer module 107. Likewise, for example, output module 106 may include an output network interface device as well as software for sending the transformed particle data output by transformer module 107 on link 150 to display device 120 or storage device 121.

Particle analyzer 110 may be any device, including a flow cytometer, that measures a signal based on a count of either photons or electrons, for example photons scattered by an excitation light projected on one or more particles under analysis detected by a PMT. Particle analyzer 110 may also be a scanning cytometer or other particle analyzer, for example and without limitation, that make measurements based on the count of fluorescence photons emitted under excitation by light beams. Storage device 111 may, in some embodiments, store the particle data output from particle analyzer 110. Particle data is input to transformer module 107 through input module 105. In one embodiment, the particle data may be received at input module 105 directly from particle analyzer 110. In another embodiment, particle data generated by particle analyzer 110 may be stored in storage device 111 before being received at input module 105.

In some embodiments of the present invention, a configuration interface 130 is coupled to the computer 101 through connection 160. Configuration interface 130 may allow the manual or programmatic configuration and management of modules including transformer module 107. For example, a user may use configuration interface 130 to manually set parameters configuring the transformation to be carried out by transformer module 107 based on the type of data to be analyzed in particle analyzer 110. Configuration interface 130 may include a local terminal and/or a remote web-based interface. Connection 160 may include a local connection or a remote connection, such as a web-based connection.

The transformed particle data output from computer 101 through output module 106, in one embodiment, may be received by display device 120. Display device 120 may be a graphical user interface capable of displaying particle analyzer data generated according to embodiments described in this disclosure. Display device 120 may include other modules necessary to receive and display and/or analyze the data output from output module 106. In another embodiment, the data output from computer 101, may be directed to a storage device 121. The transformed particle analyzer data thus stored in device 121 may later be used for further analysis or display. Storage device 121 can be coupled to computer 101 over any type of communications link. Accordingly, device 121 can be located at the same local site as computer 101 or at a different remote site. Similarly, display 120 can be located at the same local site as computer 101 or at a different remote site.

Processing Steps

Figure 2:
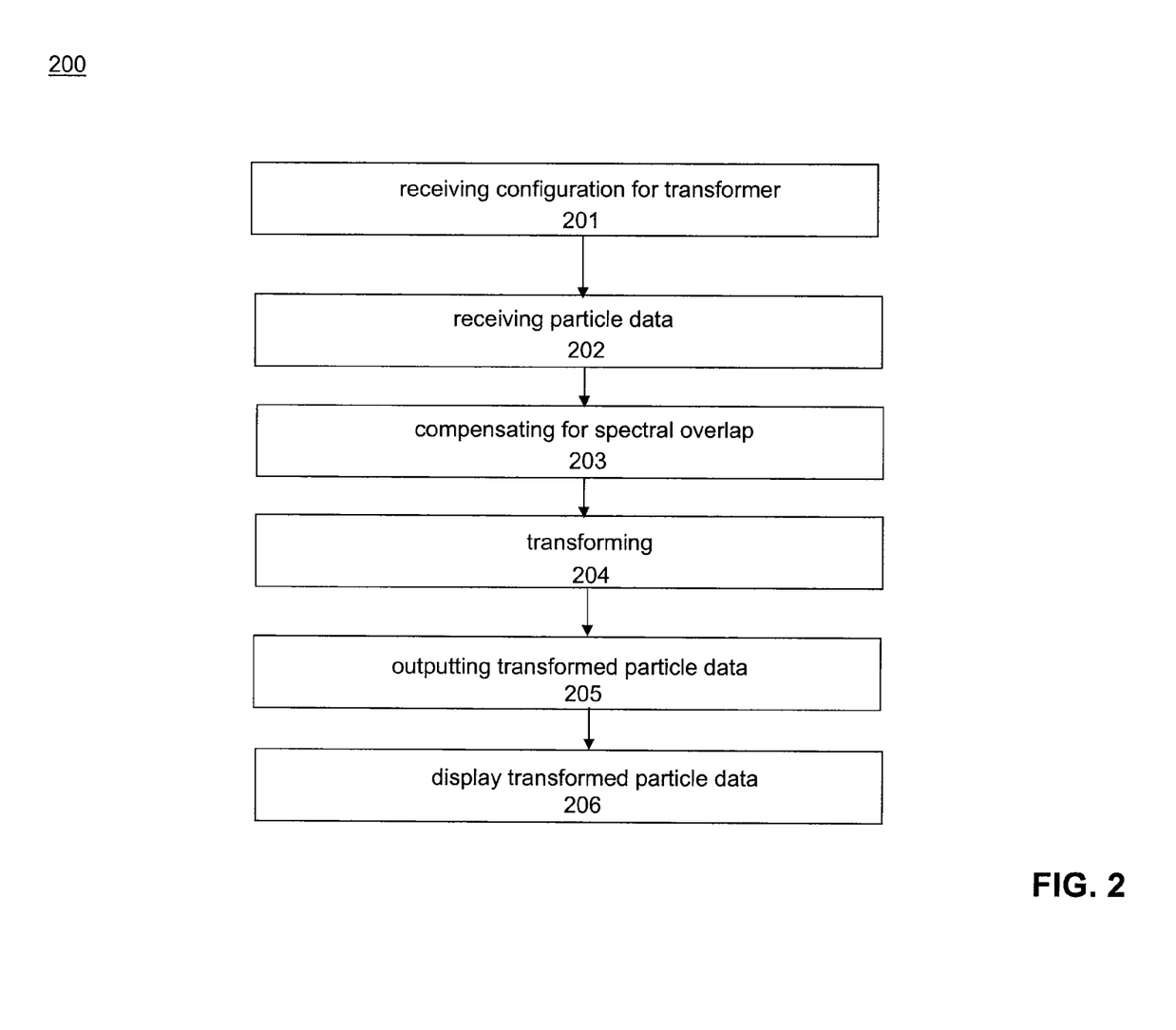
FIG. 2 is a flowchart showing the processing steps in transforming data from a particle analyzer, according to an embodiment of the present invention.

FIG. 2 is a flowchart illustrating the processing steps in an embodiment of the present invention. In step 201, configuration information is received for the transformation processing. For example, in step 201, a user may provide or select one or more mathematical functions to be used in the next transformation of particle analyzer data. In various embodiments of the present invention, mathematical equations and related parameters may be configured to tailor the transformation for particular applications. For example, when a sample of particle data has values that are mostly in the smaller ranges, the weighting functions and/or the mathematical transformation functions may be selected to highlight data points with lower values. Step 201 may include processing required to accept configuration, provided either manually by a user or programmatically, and configure a system for processing incoming particle data.

In step 202, incoming particle data from a particle analyzer is received. In some embodiments, the particle data may be received from another source, such as a storage device in which the data was stored previously. The data may be received in the form of one data point at a time, in the form of subsets of data points at a time, or in the form of all the data pertaining to a run at a time. A person skilled in the art given this description will understand that the processing steps of process 200 can be adapted accordingly—it may be interpreted as having to execute process 200 for each set of data points of particle data that is received. The particle data received in step 202, may then be compensated in step 203 to reduce the effects of spectral overlap (also called spillover). Compensation may include linear operations including subtractions from the particle data values that may result in many compensated particle data points having negative values.

Step 204 provides the transformation of the compensated or non-compensated particle data points ("particle data" unless specified otherwise) into transformed data points that, for example, can be better displayed to enable a user to meaningfully distinguish various data populations. Although most useful when applied to compensated data, it is to be understood that the teachings in this disclosure are also applicable to uncompensated particle data.

In embodiments of the present invention, particle data points, with or without being compensated, may be substituted directly as an independent variable in one or more mathematical equations that are included in the transform. The direct substitution of a particle data point (for example, a measurement for a particular type of fluorescence) for the independent variable in an equation yields a dependent variable value that may be the corresponding transformed value that is, for example, plotted on a display graph to enable the user to distinguish populations. In this way, an ability to obtain the transformed value by directly substituting the particle data point in an equation is realized. Processing in step 204 is described in greater detail with respect to FIGS. 3-6, below.

In step 205, the transformed data generated in step 204 is output. The transformed data that is output may then be displayed, stored, or subjected to further processing (step 206). In one embodiment, the transformed data may be output to a set of in-memory buffers from which another process can retrieve that data. For example, a display controller module may retrieve the transformed data from a buffer and, in step 206, display the transformed data. In another embodiment, the transformed data being output in step 205 can be directly written to a storage device, such as a computer disk drive. In yet another embodiment, the transformed data output in step 205 can be input to another module for, such as, for example, processing to further reduce effects of spectral spillover.

Figure 3:
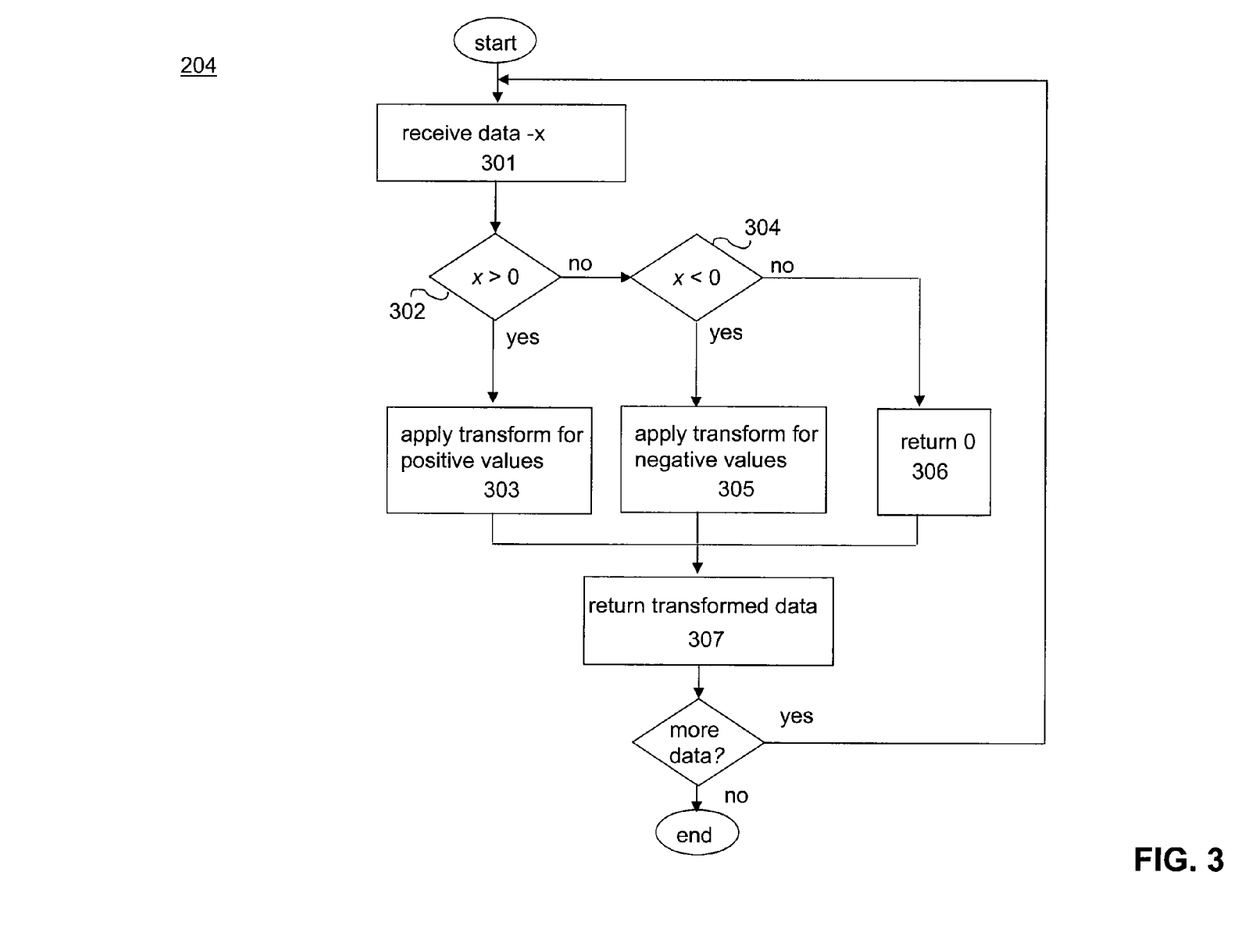
FIG. 3 is a flowchart showing more detailed processing steps in the transforming step of FIG. 2, according to an embodiment of the present invention.

FIG. 3 shows further details of the processing in step 204, in one embodiment of the present invention. In step 301, compensated data is received from step 203. The data may be received as single data points, as groups of data points, or as a group of all data points to be processed. According to an embodiment of the present invention, the data points for one display dimension is processed using step 204 based on the received data. In another embodiment, one or more additional display dimensions may be processed, by separately processing the values corresponding to each such dimension using step 204. For purposes of description, the data points to be transformed may be denoted as x. For example, in the compensated data received from step 203, x may denote data points corresponding to the fluorescence intensity of a selected fluorescence range. Each data point corresponds to the measurements obtained from one cell event. In another embodiment, the compensated data received from step 203 may include multiple data points per cell event. For example, each cell event may generate two particle data values corresponding to the measured intensities of two different fluorescence ranges.

In step 302, the value of x may be observed to be positive and if so processing is directed to step 303. If x is not positive, in step 304, it may be determined to be negative and if so, processing may be directed to step 305. In step 306, data points x that have a value of zero may be processed according to step 306, in this case, simply returning a value of zero.

Figure 4:
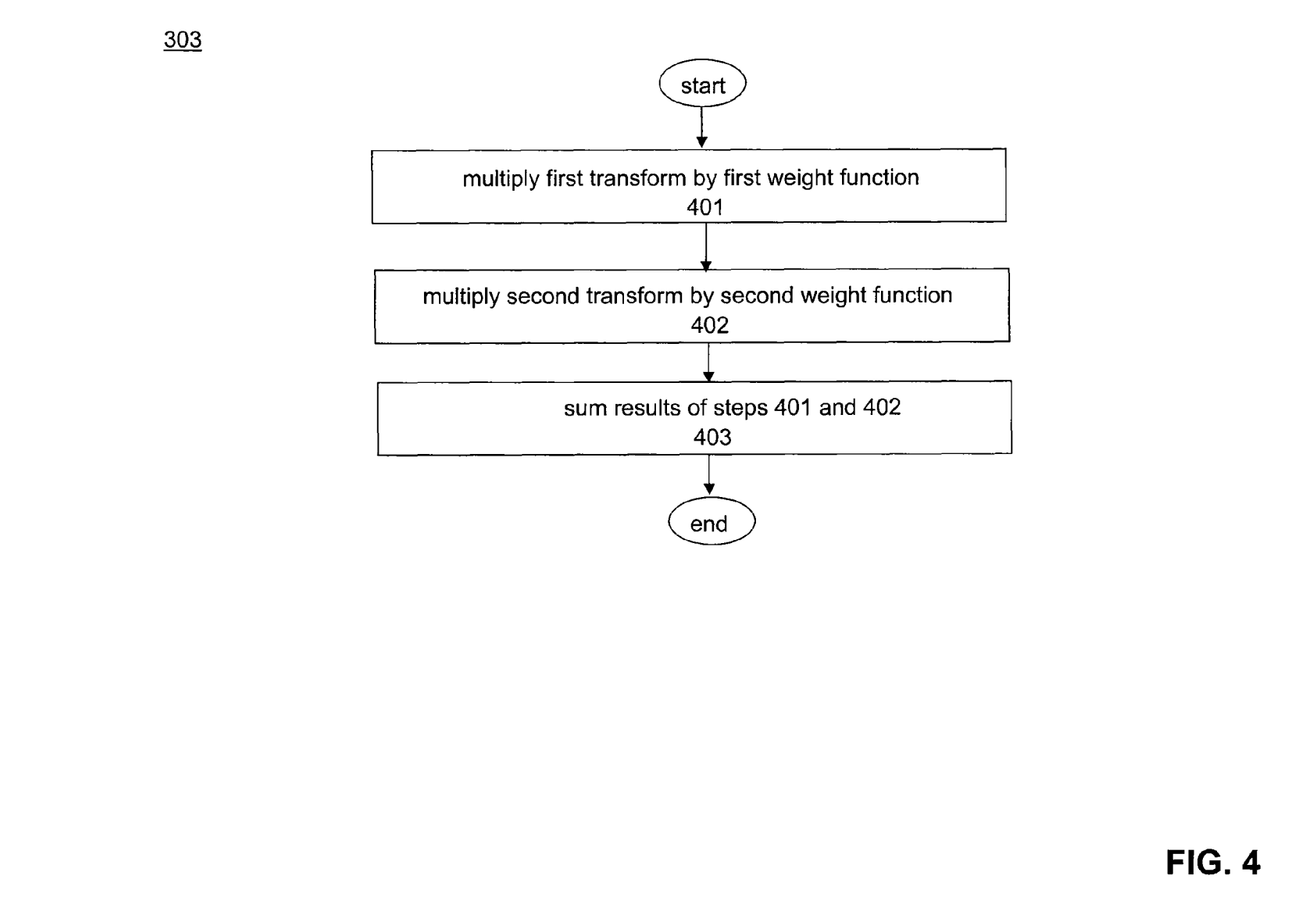
FIG. 4 shows more details of, for example, the step denoted "apply transform for positive values" shown in FIG. 3, according to an embodiment of the present invention.

In step 303, a mathematical transform designed to transform positive values may be applied to the particle data point. FIG. 4 is a flowchart showing the processing steps in applying a transform for positive values in step 303, according to one embodiment of the present invention. In step 401, a first mathematical function is multiplied by a first weight function. In step 402, a second mathematical function is multiplied by a second weight function. In step 403, the results of steps 401 and 402 are summed. Following the earlier example, when an independent particle data point x is processed according to steps 401, 402, and 403; the resulting value is y representing a transformed data point corresponding to the input value of x.

Figure 5:
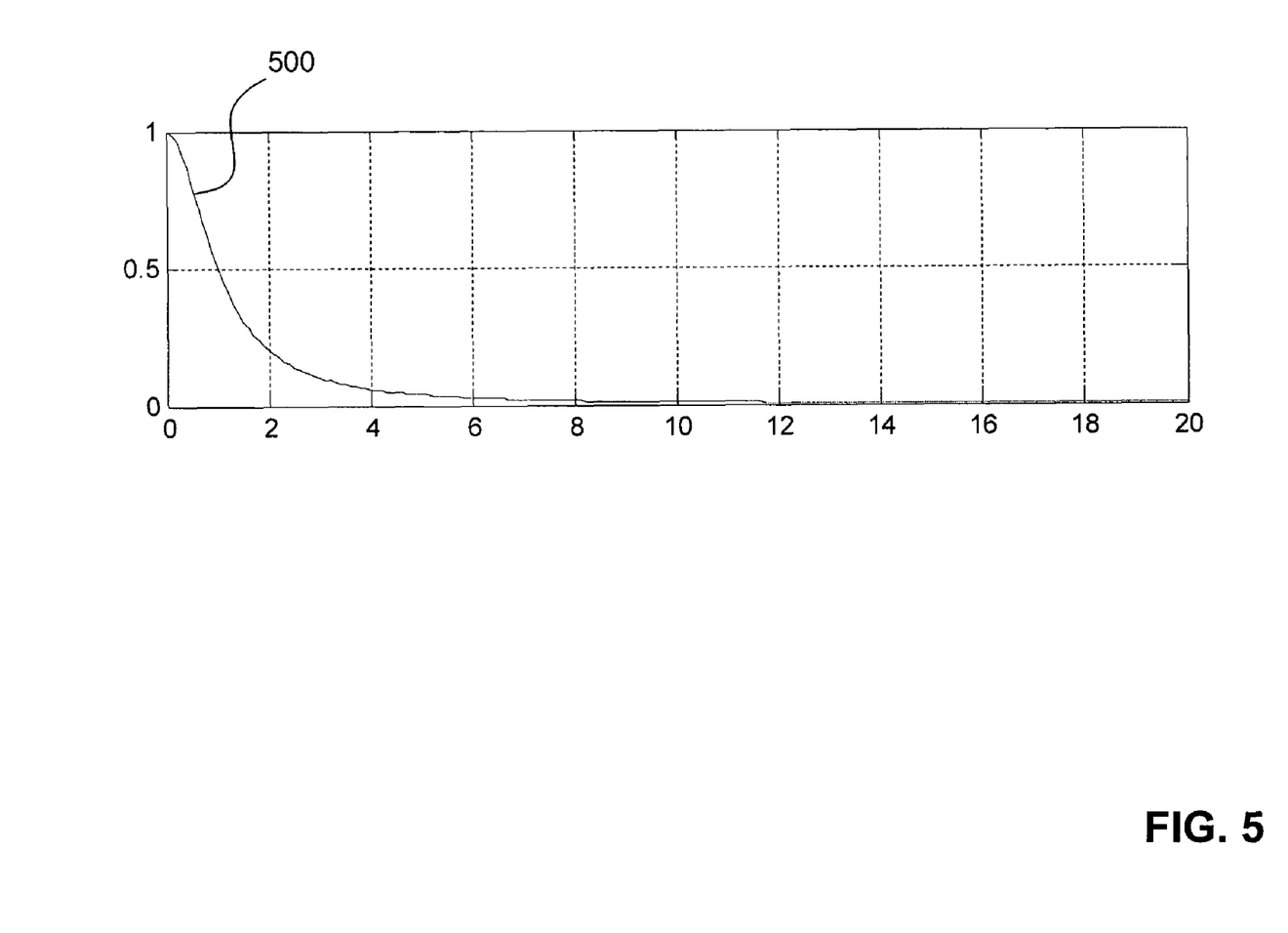
FIG. 5 shows an example first weighting function, according to an embodiment of the present invention.
Figure 6:
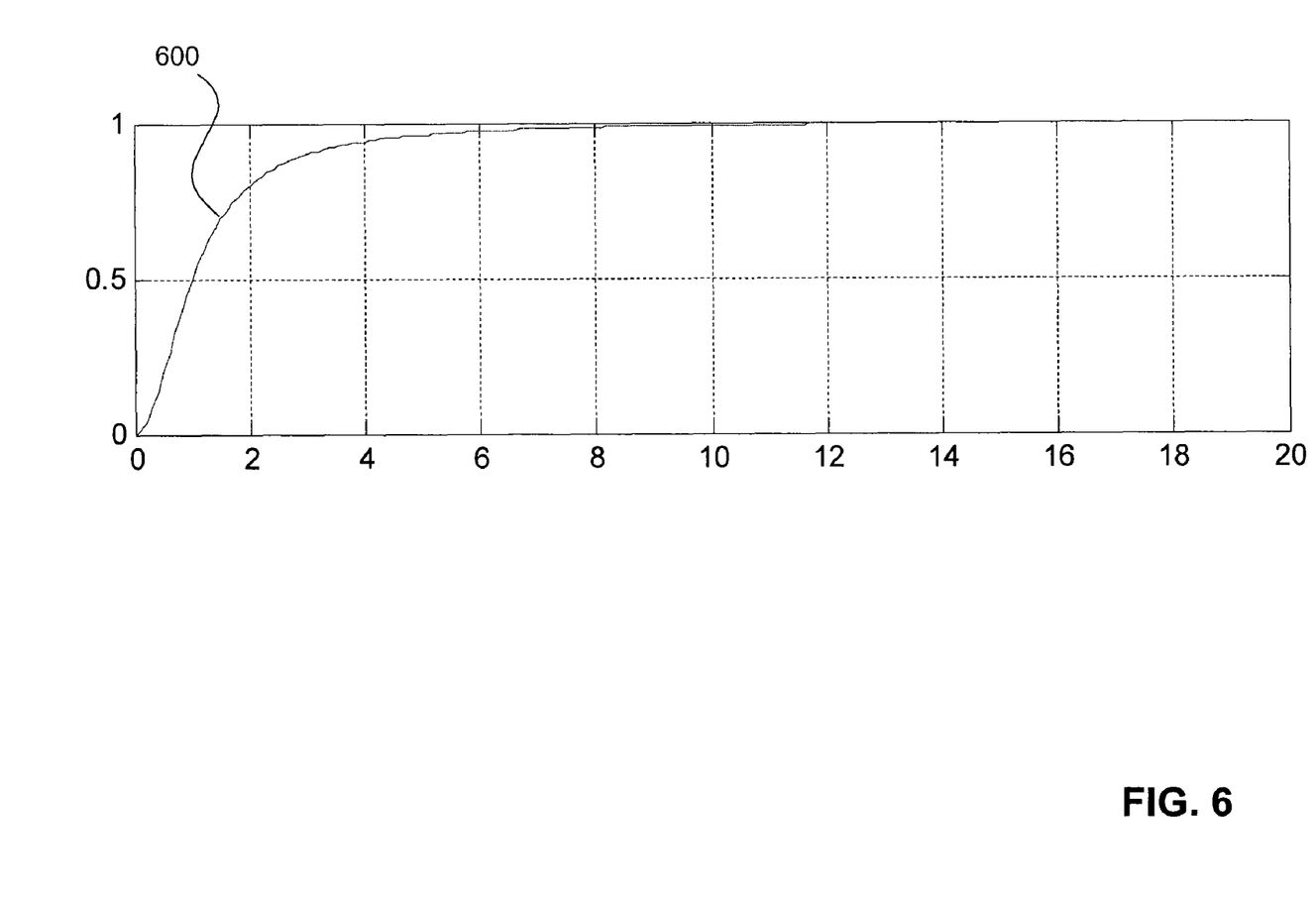
FIG. 6 shows an example second weighting function, according to an embodiment of the present invention.

In embodiments of the present invention, the second mathematical function is elected to be a logarithmic function. Example mathematical functions that may be used as a first weight function and a second weight function are shown in FIG. 5 and FIG. 6, respectively. The first mathematical function can be any continuous function. The transform, as formulated in this disclosure, gives a high degree of flexibility and can be tailored to the specific requirements of each application. The intent is to be able to have a flexible transform that will yield transformed data points that tend towards the second mathematical function (i.e., the logarithmic function) for large particle data values (i.e., large values of x or fluorescence frequency) and, towards the first mathematical function for small particle data values. The transition from the first mathematical function to the second mathematical function may be gradual and controlled by the selection of the first and second weight functions.

The first weight function is continuous over $(0, +\infty)$ and monotonically decreases from 1 to 0 when x ranges from 0 to approaching infinity. The second weight function is a continuous in $(0, +\infty)$ and monotonically increases from 0 to 1 when x ranges from 0 to approaching infinity. An example first weight function 500 is shown in FIG. 5, where the horizontal-axis indicates the particle data value and the vertical-axis gives the corresponding weight. First weight function 500, in the embodiment shown, includes an initial sharp decrease to a low value and then a more gradual decrease approaching zero. An example second weight function 600 is shown in FIG. 6, where the horizontal-axis indicates the particle data value and the vertical-axis gives the corresponding weight. Second weight function 600 includes an initial sharp increase to a high value close to the maximum one, and then a very gradual increase approaching one. Therefore, an embodiment of the present invention, that applies the example first and second weight functions shown in FIG. 5 and FIG. 6 respectively, may yield a scatter plot that has data points corresponding very closely to the first mathematical function for low particle data values, and very closely to the logarithmic function for high particle data values.

The transformed values for positive low valued particle data points, particularly those close to zero, are primarily determined by the choice of the first mathematical function. The present invention contemplates that the first mathematical function is continuous in $(0, +\infty)$.

Returning to FIG. 3, if x is determined to be negative, then a third mathematical function, one that is designed for negative values, is applies to the particle data. This invention contemplates that the third mathematical function is continuous in $(-\infty, 0]$. The third mathematical function may take any form designed to reflect the desired display pattern of data points with negative values. Further examples of first, second and third mathematical functions, and first and second weight functions are described below with respect to example transforms.

When the incoming data point x is zero, as indicated in step 306, the resulting transformed value is also zero. The transformed data point from steps 303, 305 or 306, is returned in step 307. If more particle data is to be transformed before outputting transformed data process 204 repeated.

In some embodiments, one or more of the first mathematical function, the second mathematical function, the first weight function, the second weight function, and the third mathematical function, may have the additional property of being an n-th order differential function.

EXAMPLE TRANSFORMS

Example functions that may be used to carry out data transformation in transformer module 107 are further described below. The functions are illustrative and not intended to limit the present invention.

A transformation that is designed according to an embodiment of the present invention may have the form shown in equation (1).

$$y(x) = \begin{cases} f_1(x) \cdot g(x) + f_2(x) \cdot \log(x), & x > 0 \\ h(x), & x \leq 0 \end{cases} \quad (1)$$

The transformation shown in equation (1) has the characteristics of being defined for real-values x in $(-\infty, +\infty)$, asymptotically approaching the logarithmic function when input variable x approaches $+\infty$, and being smooth in the entire function domain. This allows non-positive values to be displayed as well as positive values. In some embodiments of the present invention, the smoothness characteristic can be achieved by having a continuous n-th order differential in the function domain.

In (1), log(x) can be a logarithmic function with base 10 or other base. Weight functions $f_1(x)$ and $f_2(x)$ can each be a function defined in the range $(0, +\infty)$ with continuous n-th order differential. For example, $f_1(x)$ may monotonically decrease from 1 to 0 in $(0, +\infty)$ with $$\underset{x \to 0}{Limit} f_1(x) = 1$$

as shown in FIG. 5, and $f_2(x)$ may monotonically increase from 0 to 1 in $(0, +\infty)$ with $$\underset{x\to 0}{Limit}\, f_2(x) = 0$$

as shown in FIG. 6.

Also in (1), the first mathematical function, i.e., g(x), is a continuous n-th order differential function in the range (0, +∞) with desired behavior approaching zero. The effect of the weight functions $f_1(x)$ and $f_2(x)$ is that y(x) behaves like g(x) close to zero when x is positive and behaves like log(x) when x is positive and large. The third mathematical function, i.e., h(x), is a continuous n-th order differential function in (−∞, 0] that makes the n-th order differential of y(x) continuous in (−∞, +∞).

Equation (1) can be further tuned for specific applications that demand additional characteristics, such as, for example and without limitation, symmetry around 0 for the transformation, i.e., having y(x)=−y(−x). A transformation having this added characteristic may be illustrated as equation (2) below.

$$y(x) = \begin{cases} f_1(x)\cdot g(x) + f_2(x)\cdot \log(x), & x > 0 \\ 0, & x = 0 \\ -[f_1(-x)\cdot g(-x) + f_2(-x)\cdot \log(-x)], & x < 0 \end{cases} \quad (2)$$

The weight functions $f_1(x)$ and $f_2(x)$ can take many forms. Some example pairings of weight functions are shown in equations (3), (4) and (5).

$$\begin{cases} f_1(x) = \dfrac{1}{\cosh(a\cdot x)}, & a > 0 \\ f_2(x) = \tanh(b\cdot x), & b > 0 \end{cases} \quad (3)$$

$$\begin{cases} f_1(x) = \dfrac{2}{1 + e^{a\cdot |x|}} \\ f_2(x) = \dfrac{e^{a\cdot x} - 1}{e^{a\cdot x} + 1} \end{cases},\, a > 0 \quad (4)$$

$$\begin{cases} f_1(x) = \dfrac{c^a}{c^a + x^a} \\ f_2(x) = \dfrac{x^a}{c^a + x^a} \end{cases},\, a > 0, c > 0 \quad (5)$$

where a, b, and c are positive real numbers.

As an example, when (5) is selected as $f_1(x)$ and $f_2(x)$, the transform can be written as in equation (6).

$$y(x; a, c) = \begin{cases} \dfrac{c^a}{c^a + x^a}\cdot g(x) + \dfrac{x^a}{c^a + x^a}\cdot \log(x), & x > 0 \\ 0, & x = 0 \\ \dfrac{-c^a}{c^a + (-x)^a}\cdot g(-x) - \dfrac{(-x)^a}{c^a + (-x)^a}\cdot \log(-x), & x < 0 \end{cases} \quad (6)$$

where a and c are positive real numbers.

The transformation shown in equation (6), in addition to the characteristics of the basic transformation (1), has the following characteristics: the sum of $f_1(x)$ and $f_2(x)$ is 1 in (0, +∞); $f_1(x)$ and $f_2(x)$ are equal at x=c, meaning that the g(x) and the logarithmic functions are weighted evenly at x=c; and parameter "a" correlates with the transition speed from the g(x)-dominant zone (i.e., low x) to logarithm-dominant zone (i.e., high x). The larger the value of "a", the faster the transition and the shorter the transition zone is.

In another example embodiment of the present invention, the first mathematical function, i.e., g(x), is an n-th order power function with a scaling factor "d". To reduce the number of parameters to be determined, only the highest order power term is kept in following example form. So equation (6) can be rewritten as equation (7) below.

$$y(x; a, c, d, n) = \begin{cases} \dfrac{c^a}{c^a + x^a}\cdot d\cdot x^n + \dfrac{x^a}{c^a + x^a}\cdot \log(x), & x > 0 \\ 0, & x = 0 \\ \dfrac{-c^a}{c^a + (-x)^a}\cdot d\cdot (-x)^n - \dfrac{(-x)^a}{c^a + (-x)^a}\cdot \log(-x), & x < 0 \end{cases} \quad (7)$$

where a, c, d, and n are positive real numbers.

As formulated in equation (7), the transform y(x) has, in addition to the characteristics of equation (6), the added characteristic of having parameters d and n together shape the behavior of y(x) around zero.

Figure 7:
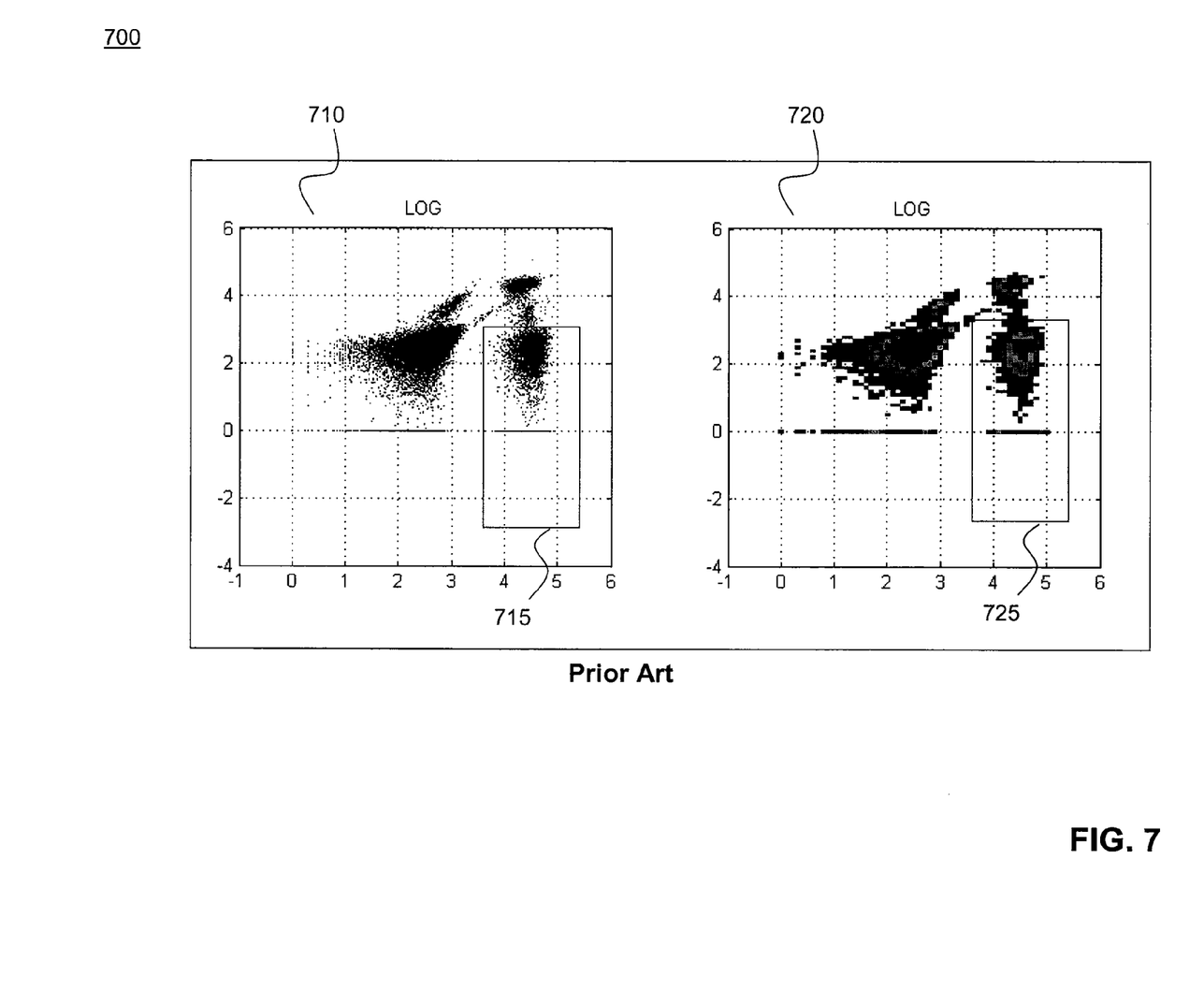
FIG. 7 shows a scatter plot (left) and density plot (right) displaying sample data using an existing logarithmic display method.
Figure 8:
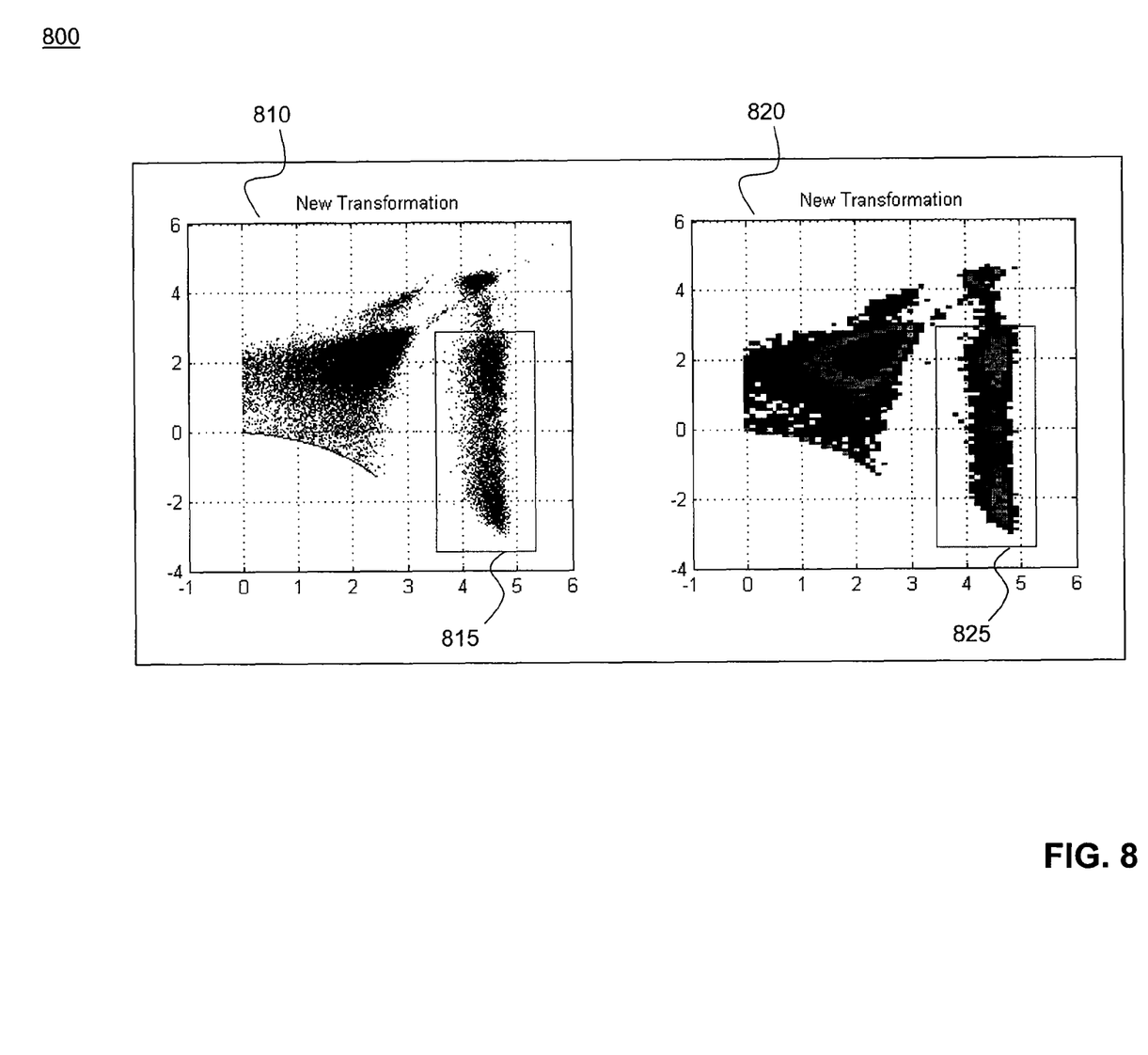
FIG. 8 shows a scatter plot (left) and density plot (right) displaying the same sample data as in FIG. 7, using an embodiment of the present invention.
Figure 9:
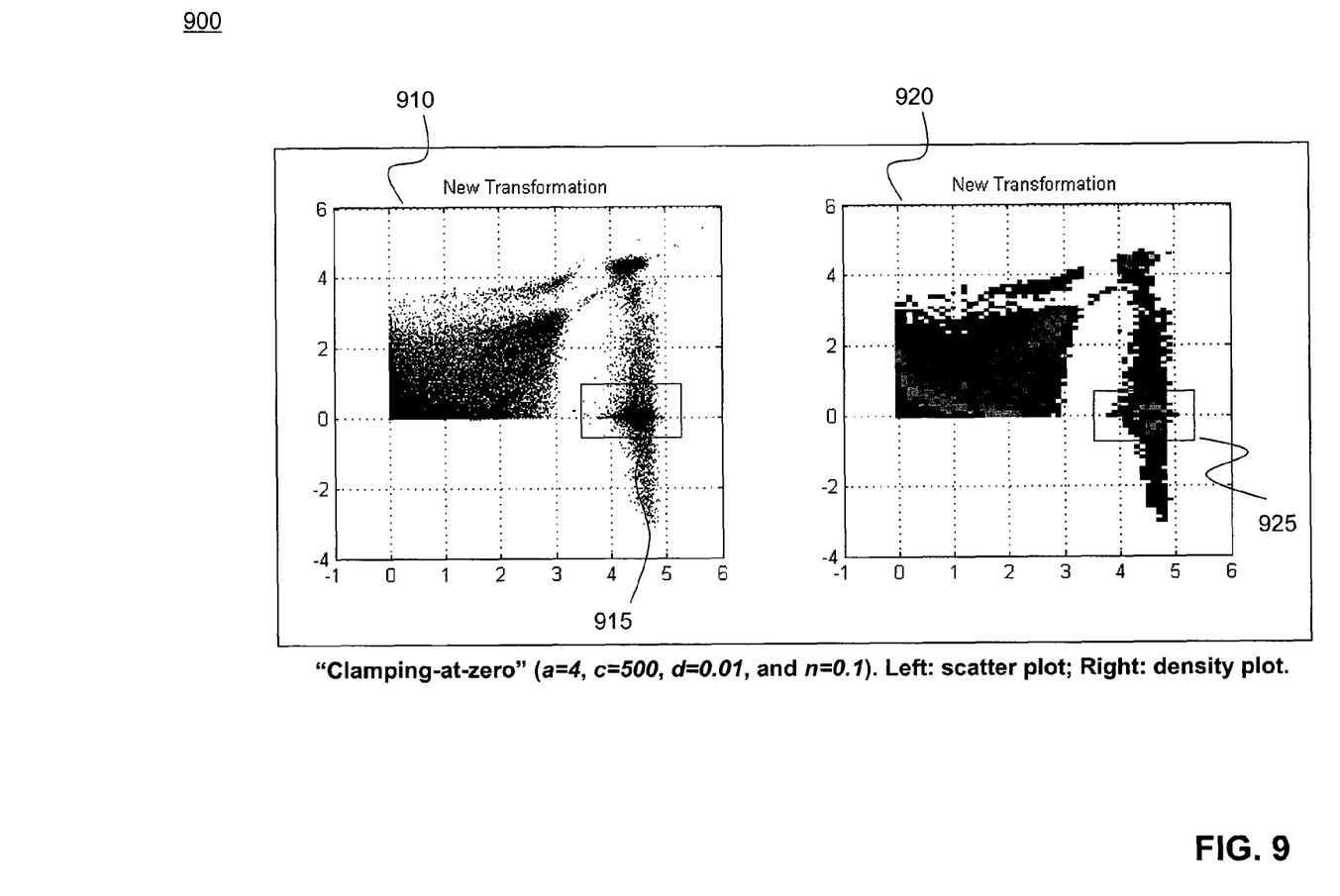
FIG. 9 is a scatter plot (left) and density plot (right) displaying the effect of "clamping at zero" when using an embodiment of the present invention with improper parameter configuration.
Figure 10:
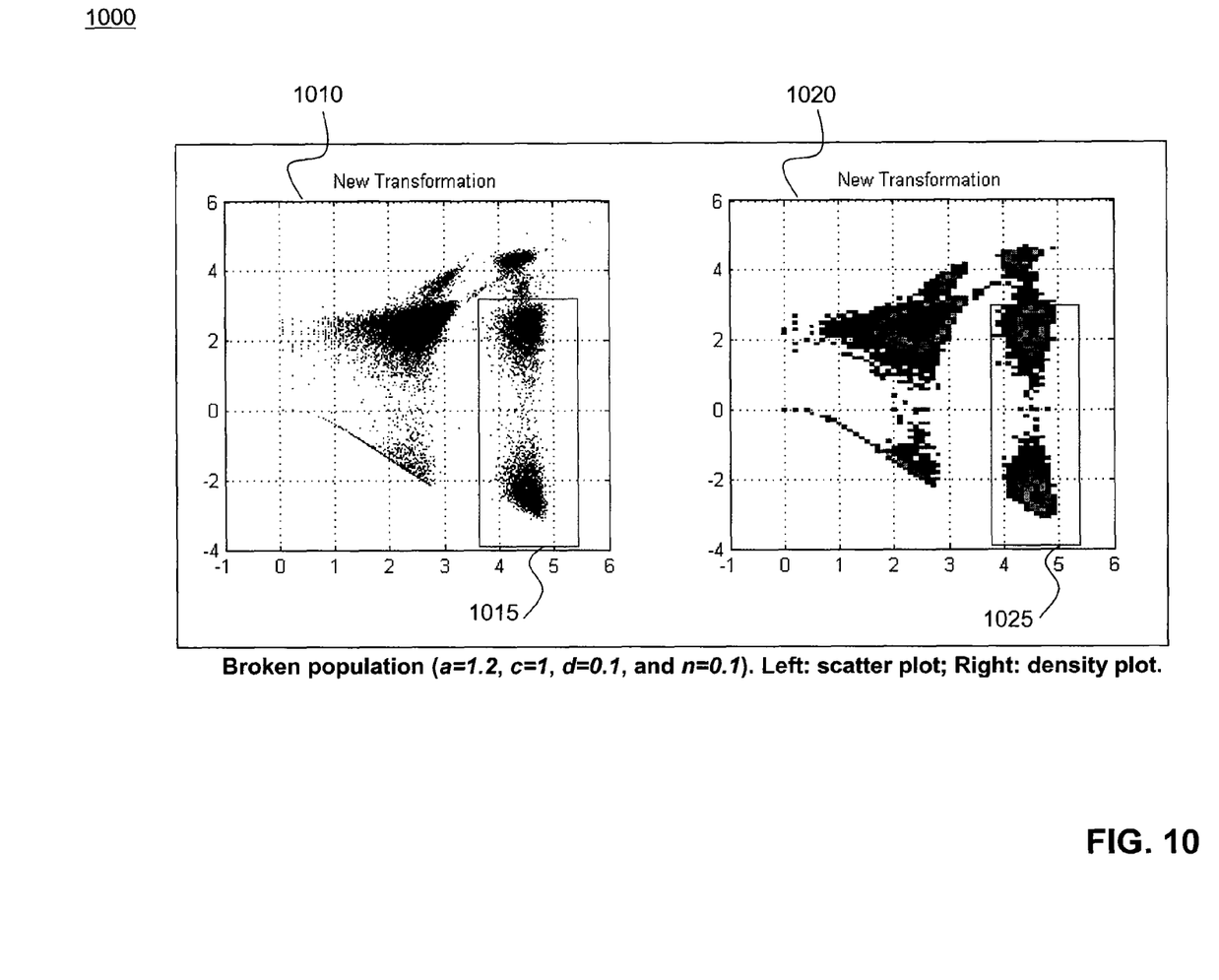
FIG. 10 is scatter plot (left) and density plot (right) displaying the effect of "broken population" when using an embodiment of the present invention with improper parameter configuration.

In FIG. 7, an over-compensated sample of particle data is displayed using a logarithmic transformation. FIGS. 7-10 depict FL2 measurements on the horizontal-axis and FL3 measurements on the vertical-axis. In the scatter plot 710 and the density plot 720, most events in the lower right (in the area enclosed by boxes 715 and 725, respectively) are negative due to overcompensation. These negative-valued events do not have valid logarithmic values. Therefore, as shown in 710 and 720, these negative-valued events are collapsed on a value of 0, artificially damaging information of the population. This missing population of negative-valued events introduces difficulties in color compensation and can potentially cause erroneous results. FIG. 8 shows a transformation according to an embodiment of the present invention. In contrast to FIG. 7, the transformed particle data in FIG. 8 (as shown in the scatter plot 810 and the density plot 820), including the negatively valued event population, is displayed with substantial clarity. For example, the areas enclosed by boxes 815 and 820 clearly display negative event populations. The presence of the negatively valued population informs the operation when the overcompensation occurs and to what levels the sample is over compensated. Scatter plot 810 and density plot 820 are generated with the transform represented in equation (7) with the parameters a=1.2, c=100, d=0.01, and n=0.1.

The parameters in the equation (7), a, c, d, and n determine the behavior of y(x) jointly. If they are not chosen appropriately, unexpected results may happen. If the slope of y(x) around zero is too small, "clamping-at-zero" may occur, in which many non-zero x's have y values of zero. As a result, the event population is squeezed towards y=0, artificially creating a high-density region as shown, for example, in the areas enclosed by box 915 of scatter plot 910 and box 925 of density plot 920 in FIG. 9. Another side effect of improper parameterization may be a "broken population." A broken population occurs when the slope of y(x) around zero is too steep so that a tiny change in x results in a disproportionately large change in y(x). Consequently, a connected population may be broken and artificial populations may be created, as shown, for example, in the areas enclosed by box 1015 of scatter plot 1010 and box 1025 of density plot 1020 in FIG. 10.

Conclusion

According to a feature, a transformation as disclosed herein may enable the direct calculation of the data points to be displayed by providing as input the particle data points including compensated particle data points. A closed form of the transformation, as disclosed herein, can avoid the computation-intensiveness and uncertainty due to potential non-convergence involved in root-finding operations, and the inflexibility and inaccuracies that may be involved with using lookup-tables to derive transformed data points based on the input particle data points.

In a further feature, the transformation disclosed herein also offers the flexibility of using a transform specifically suited for a particular application. For each application, particular transform functions and parameters may be known as particularly suitable. In equation (7), for example, the parameters a, c, d, and n determines the behavior of y(x) jointly. If these parameters are not chosen appropriately, unexpected results, such as, clamping-at-zero and broken populations, can occurs as noted above. Proper selection of values, however, enables the use of the transformation disclosed herein to transform particle data to an improved useful form.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A computer-implemented method for analyzing, for each particle, particle data from a particle analyzer, the method comprising the steps of:
   receiving particle data for each particle at a computer;
   transforming the particle data for each particle with the computer using at least one transform that provides:
   a first transformation according to a weighted combination of a first mathematical function and a logarithmic function for positive particle data values, wherein said transformation corresponds to the first mathematical function for positive particle data values approaching zero; and
   a second transformation corresponding to a second mathematical function for negative particle data values, to generate transformed data; and
   outputting the transformed data,
   wherein the at least one transform comprises the steps of:
   (a) multiplying the first mathematical function by a first weight function;
   (b) multiplying the logarithmic function by a second weight function; and
   (c) summing the results of steps (a) and (b), and
   wherein the first weight function is continuous over a range in particle data values (0, +∞), and monotonically decreases from 1 to 0 over a range (0, +∞) in particle data values.

2. A computer-implemented method for analyzing, for each particle, particle data from a particle analyzer, the method comprising the steps of:
   receiving particle data for each particle at a computer;
   transforming the particle data for each particle with the computer using at least one transform that provides:
   a first transformation according to a weighted combination of a first mathematical function and a logarithmic function for positive particle data values, wherein said transformation corresponds to the first mathematical function for positive particle data values approaching zero; and
   a second transformation corresponding to a second mathematical function for negative particle data values, to generate transformed data; and
   outputting the transformed data,
   wherein the at least one transform comprises the steps of:
   (a) multiplying the first mathematical function by a first weight function;
   (b) multiplying the logarithmic function by a second weight function; and
   (c) summing the results of steps (a) and (b), and
   wherein the second weight function is continuous over a range in particle data values (0, +∞), and monotonically increases from 0 to 1 over a range (0, +∞) in particle data values.

3. A computer-implemented method for analyzing, for each particle, particle data from a particle analyzer, the method comprising the steps of:
   receiving the particle data for each particle at a computer;
   transforming the particle data for each particle with the computer using at least one transform that provides:
   a first transformation according to a weighted combination of a first mathematical function and a logarithmic function for positive particle data values, wherein said transformation corresponds to the first mathematical function for positive particle data values approaching zero; and
   a second transformation corresponding to a second mathematical function for negative particle data values, to generate transformed data; and
   outputting the transformed data,
   wherein the second mathematical function is an odd-symmetric function of the first mathematical function over a range (−∞,0) in particle data values.

4. A system for transforming particle data generated by a particle analyzer, for each particle analyzed, comprising:
   a computer configurable to be coupled to the particle analyzer, wherein the computer comprises:
   a transformer module that provides:
   a first transformation of particle data for each particle analyzed according to a weighted combination of a first mathematical function and a logarithmic function for positive particle data values, wherein the first transformation corresponds to the first mathematical function for positive particle data values approaching zero; and
   a second transformation corresponding to a second mathematical function for negative particle data values, wherein the second mathematical function is an odd-symmetric function of the first mathematical function over a range (−∞,0) in particle data values, to generate transformed data.

5. A computer program product comprising a non-transitory computer readable medium having control logic stored therein for causing a computer to transform particle data for each particle of a plurality of particles, said control logic comprising:
   a first computer readable program code that enables the computer to perform:
   a first transformation of data for each particle of the plurality of particles according to a weighted combination of a first mathematical function and a logarithmic function for positive particle data values, wherein the first transformation corresponds to the first mathematical function for positive particle data values approaching zero; and a second transformation corresponding to a second mathematical function for negative particle data values, wherein the second mathematical function is an odd-symmetric function of the first mathematical function over a range $(-\infty,0)$ in particle data values, to generate transformed data.

6. A system for transforming particle data generated by a particle analyzer, for each particle analyzed, comprising:
  a computer configurable to be coupled to the particle analyzer, wherein the computer comprises:
  a transformer module that provides:
    a first transformation of particle data for each particle analyzed according to a weighted combination of a first mathematical function and a logarithmic function for positive particle data values, wherein the first transformation corresponds to the first mathematical function for positive particle data values approaching zero; and
    a second transformation corresponding to a second mathematical function for negative particle data values, and
  wherein at least one transformation comprises the steps of:
    (a) multiplying the first mathematical function by a first weight function;
    (b) multiplying the logarithmic function by a second weight function; and
    (c) summing the results of steps (a) and (b), and
  wherein the first weight function is continuous over a range in particle data values $(0, +\infty)$, and monotonically decreases from 1 to 0 over a range $(0, +\infty)$ in particle data values, to generate transformed data.

7. A system for transforming particle data generated by a particle analyzer, for each particle analyzed, comprising:
  a computer configurable to be coupled to the particle analyzer, wherein the computer comprises:
  a transformer module that provides:
    a first transformation of particle data for each particle analyzed according to a weighted combination of a first mathematical function and a logarithmic function for positive particle data values, wherein the first transformation corresponds to the first mathematical function for positive particle data values approaching zero; and
    a second transformation corresponding to a second mathematical function for negative particle data values,
  wherein at least one transformation comprises the steps of:
    (a) multiplying the first mathematical function by a first weight function;
    (b) multiplying the logarithmic function by a second weight function; and
    (c) summing the results of steps (a) and (b), and
  wherein the second weight function is continuous over a range in particle data values $(0, +\infty)$, and monotonically increases from 0 to 1 over a range $(0, +\infty)$ in particle data values, to generate transformed data.

8. A computer program product comprising a non-transitory computer readable medium having control logic stored therein for causing a computer to transform particle data for each particle of a plurality of particles, said control logic comprising:
  a first computer readable program code that enables the computer to perform:
    a first transformation of data for each particle of the plurality of particles according to a weighted combination of a first mathematical function and a logarithmic function for positive particle data values, wherein the first transformation corresponds to the first mathematical function for positive particle data values approaching zero; and
    a second transformation corresponding to a second mathematical function for negative particle data values,
  wherein at least one transformation comprises the steps of:
    (a) multiplying the first mathematical function by a first weight function;
    (b) multiplying the logarithmic function by a second weight function; and
    (c) summing the results of steps (a) and (b), and
  wherein the first weight function is continuous over a range in particle data values $(0, +\infty)$, and monotonically decreases from 1 to 0 over a range $(0, +\infty)$ in particle data values, to generate transformed data.

9. A computer program product comprising a non-transitory computer readable medium having control logic stored therein for causing a computer to transform particle data for each particle of a plurality of particles, said control logic comprising:
  a first computer readable program code that enables the computer to perform:
    a first transformation of data for each particle of the plurality of particles according to a weighted combination of a first mathematical function and a logarithmic function for positive particle data values, wherein the first transformation corresponds to the first mathematical function for positive particle data values approaching zero; and
    a second transformation corresponding to a second mathematical function for negative particle data values,
  wherein at least one transformation comprises the steps of:
    (a) multiplying the first mathematical function by a first weight function;
    (b) multiplying the logarithmic function by a second weight function; and
    (c) summing the results of steps (a) and (b), and
  wherein the second weight function is continuous over a range in particle data values $(0, +\infty)$, and monotonically increases from 0 to 1 over a range $(0, +\infty)$ in particle data values, to generate transformed data.

* * * * *